United States Patent [19]

Pelix et al.

[11] Patent Number: 4,817,120
[45] Date of Patent: Mar. 28, 1989

[54] MULTICHANNEL X-RAY SPECTROMETER

[76] Inventors: Evgeny A. Pelix, Piskarevsky prospekt, 35, kv. 46; Valter I. Zakharchenko, Krasnogvardeisky prospekt, 30, kv. 34; Svyatoslav M. Sergeev, ulitsa Dekabristov, 43, kv. 25; Leonid N. Lozovoi, ulitsa Blokhina 4, kv. 52; Vladimir A. Gudovskikh, ulitsa Ryleeva, 24, kv. 8; Sergei B. Krasilnikov, prospekt Shvernika, 10, korpus 1, kv. 175; Evgeny A. Kornev, ulitsa Vavilovvkh 4, korpus 1, kv. 448; Sergei N. Markov, prospekt Nauki, 20, kv. 50; Arkady L. Farberg, ulitsa Favorskogo, 18, kv. 41; Vitaly A. Khilkevich, Krasnogvardeisky prospekt, 29/10, kv. 54, all of Leningrad, U.S.S.R.

[21] Appl. No.: 164,461

[22] Filed: Mar. 4, 1988

[51] Int. Cl.[4] ................................. G01N 23/223
[52] U.S. Cl. ................................. 378/45; 378/84; 378/85
[58] Field of Search .................. 378/45, 49, 82–85

[56] References Cited

U.S. PATENT DOCUMENTS

| | | | |
|---|---|---|---|
| 2,540,821 | 2/1951 | Harker | 378/49 |
| 3,198,944 | 8/1965 | Furbee | 378/49 |
| 3,213,278 | 10/1965 | Spielberg | 378/49 |
| 3,486,021 | 12/1969 | Honme et al. | 378/83 |
| 4,091,282 | 5/1978 | Anisovich et al. | 378/45 |

FOREIGN PATENT DOCUMENTS 0108746  7/1982  Japan ........................ 378/45

OTHER PUBLICATIONS

"Convex Curved Crystal X-Ray Spectrograph", by Birks Review Scientific Instruments, vol. 41, No. 8, 8/1970.
ARL, US, ARL 7200 S, 1981—without translation.
XIII Vsesojuznoe Soveschanie po Rentgenovskoi i Elektronnoi . . . Mnogokanalny, pp. 245–246—without translation.

*Primary Examiner*—Bruce C. Anderson
*Assistant Examiner*—John C. Freeman
*Attorney, Agent, or Firm*—Lilling & Greenspan

[57] ABSTRACT

A multichannel X-ray spectrometer comprises, in each spectrometric channel, individual holders for a focusing crystal analyzer and for an outlet slit, which are placed on a base and made as cylindrical supports equipped with slit locks. Cylindrical sockets are provided on the end face of the base and arranged adequately with respective cylindrical supports. Each socket has its own cylindrical support placed therein so that the slit locks envelop side surfaces of the base. The axes of the cylindrical supports coincide with the central generating line of the crystal analyzer and the outlet slit, respectively, and are spaced apart to a distance equal to $2R(1-2\delta)\sin\theta$, where R is the radius of the focusing circle of the focusing crystal analyzer, $\delta$ is the mosaic structure factor, and $\theta$ is the Bragg reflection angle. The end face of the base between the cylindrical sockets has an angle equal to $180°-2\theta$.

1 Claim, 2 Drawing Sheets

MULTICHANNEL X-RAY SPECTROMETER

BACKGROUND OF THE INVENTION

1. Field of the Invention

This invention relates to X-ray spectrometers for qualitative and quantitative analysis of element composition of substances and, in particular, it relates to multichannel X-ray spectrometers.

The invention can be used in many fields of science and technology, such as physics, chemistry, biology, metallurgy, geology, to deal with applied problems and fundamental scientific investigations.

2. Description Of The Prior Art

Known in the art is a multichannel X-ray spectrometer comprising an X-ray tube, a specimen holder placed opposite the X-ray tube, and spectrometric channels arranged around the X-ray tube and comprising, located one after another in the direction of the X-radiation, inlet slits, focusing crystal analyzers, and outlet slits mounted, like the focusing crystal analyzers, in individual holders resting on a base, and detectors of X-radiation (ARL, US, ARL 72000 S,1981).

In this spectrometer, individual holders are metal plates having one concave surface. These individual holders are placed on the base and arranged along the focusing circle of the focusing crystal analyzers by means of adjusting screws and secured in their respective positions.

This means that adjustment of spectrometric channels is actually mechanical shifting, with respect to one another, of individual holders for crystal analyzers and outlet slits. This is definitely a serious disadvantage because spectrometric channels become too complicated in design and, consequently, the spectrometer itself is too complex. Adjustment of the channels and spectrometer is a labor-consuming process.

Also known in the art is a multichannel X-ray spectrometer comprising an X-ray tube, a specimen holder placed opposite the X-ray tube, and spectrometric channels arranged around the X-ray tube and comprising, arranged one after another in the direction of X-radiation, inlet slits, focusing crystal analyzers, and outlet slits mounted, like the focusing crystal analyzers, in individual holders on a base, and detectors of X-radiation (XIII Vsesojuznoe soveschanie po rentgenovskoi i elektronnoi spektroskopii, Report abstracts, 1981, Lvov, I.P. Zhizhin et al. Spektrometr rentgenovsky mnogokanalny, pp. 245-246).

In this prior art spectrometer, individual holders for crystal analyzers and for the outlet slits are installed on the lateral base surface in each spectrometric channel.

This spectrometer is deficient in that, with the radius of the focusing circle of the focusing crystal analyzers in each channel being about 100 mm, only six channels can be arranged around the X-ray tube. A greater number of spectrometric channels can only be achieved in this spectrometer by placing two holders for crystal analyzers and, respectively, two holders for outlet slits on the base, one upon the other. This makes adjustment of spectrometric channels and, consequently, of the spectrometer a difficult job. Moreover, the spectrometric channels become much larger in size as does the spectrometer itself.

SUMMARY OF THE INVENTION

It is an object of this invention to simplify adjustment of spectrometric channels and, consequently, of the spectrometer as such.

Another object of the invention is to reduce the size of spectrometric channels and, consequently, of the spectrometer as such.

This is achieved by a multichannel X-ray spectrometer comprising an X-ray tube, a specimen holder placed opposite the X-ray tube, and spectrometric channels arranged around the X-ray tube and further comprising, arranged in series one after another in the direction of the X-radiation, inlet slits, focusing crystal analyzers, and outlet slits mounted, like the focusing crystal analyzers, in individual holders resting on a base, and X-radiation detectors. According to the invention, each individual holder for the focusing crystal analyzer and for the outlet slit is made as a cylindrical support having slit locks, the butt surface of each spectrometric channel is provided with cylindrical sockets arranged adequately with respective cylindrical supports, each cylindrical support being fit in each cylindrical socket so that slit locks envelop the lateral surfaces of the base, the axes of the cylindrical supports of individual holders for the focusing crystal analyzer and for the outlet slit coinciding with the central generating line of the crystal analyzer and of the outlet slit, respectively, being spaced apart to a distance equal to or less than $2R(1-2\delta) \sin \theta$, where R is the radius of the focusing circle of a crystal analyzer;

$\delta$ is mosaic structure factor of a focusing crystal analyzer;

$\delta$ is the Bragg reflection angle, and the butt end surface of the base between cylindrical sockets is shaped at an angle equal to $180°-2\theta$.

This design configuration of a multichannel X-ray spectrometer makes it possible to reduce the adjustment of the spectrometer during its assembly to setting the distance between the crystal analyzer and the outlet slit and respective turn of the crystal analyzer to the Bragg angle, and to make the spectrometer much smaller.

BRIEF DESCRIPTION OF DRAWINGS

These and other objects of the invention will become apparent from the following description of the invention and accompanying drawings wherein.

DESCRIPTION OF THE PREFERRED EMBODIMENT

Figure 1:
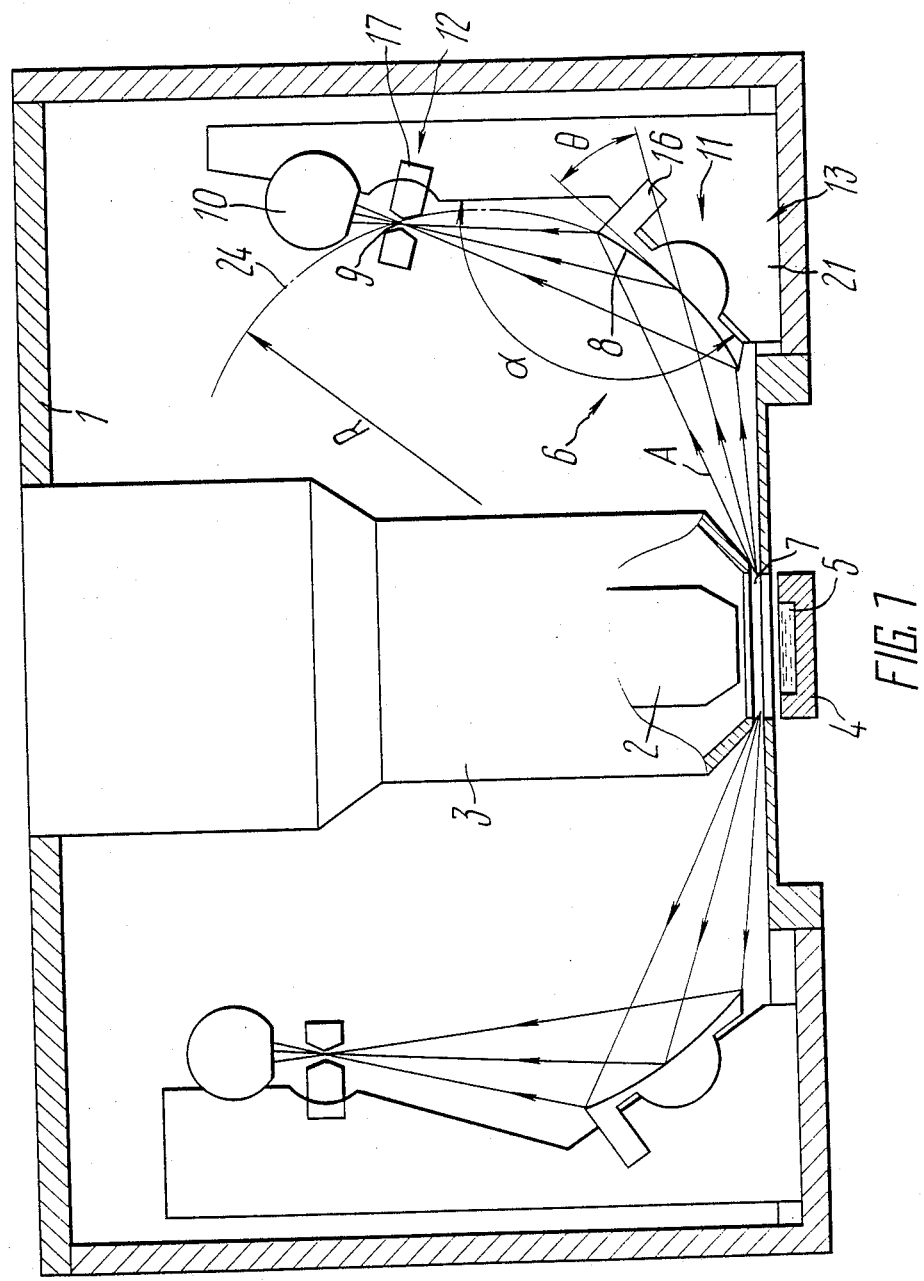
FIG. 1 shows a schematic of a multichannel X-ray spectrometer as a partially fragmented longitudinal section, according to the invention.

A multichannel X-ray spectrometer, according to the invention, includes a housing 1 (FIG. 1) accommodating an X-ray tube 2 enclosed in a shell 3. A holder 4 for a specimen 5 to be studied is placed opposite the X-ray tube 2. The housing 1 also accommodates spectrometric channels 6 arranged around the X-ray tube 2. These spectrometric channels 6 include inlet slits 7, focusing crystal analyzers 8, outlet slits 9, and X-radiation detectors 10, all placed one after another in the direction A of x-radiation.

Focusing crystal analyzers 8 and outlet slits 9 are mounted in individual holders 11 and 12 respectively, which are resting on a base 13 secured on the bottom of the housing 1.

Figure 2:
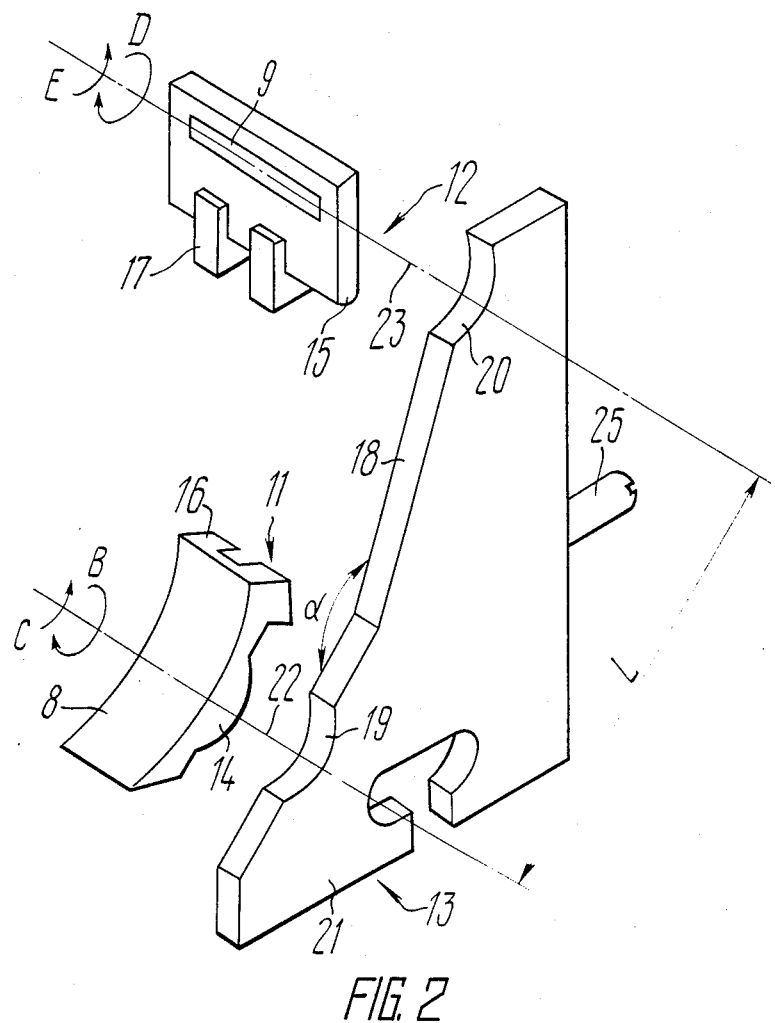
FIG. 2 shows an axonometric view of a base and holders for focusing crystal analyzers and outlet slits of the spectrometer shown in FIG. 1, according to the invention.

Each of the indiviudal holders 11 (FIG. 2) and 12 are made, respectively, as cylindrical supports 14 and 15 featuring slit locks 16 and 17.

Cylindrical sockets 19 and 20 are provided on an end face 18 of the base 13. These sockets 19 and 20 accommodate the cylindrical supports 14 and 15 respectively. Each cylindrical socket 19 and 20 accommodates its own cylindrical support: support 14 for the socket 19, and support 15 for the socket 20 so that slit locks 16 and 17 envelop side faces 21 of the base 13 as shown in FIG. 1.

Axes 22 (FIG. 2) and 23 of the cylindrical supports 14 and 15 coincide with the central generatrix of the focusing crystal analyzer 8 and the outlet slit 9, respectively, being spaced apart to a distance L equal to $2R(1-2\delta)\sin \theta$, where R is the radius of a focusing circle 24 (FIG. 1) of the focusing crystal analyzer 8.

$\delta$ is the mosaic structure factor of the focusing crystal analyzer 8, and $\theta$ is the Bragg reflection angle.

The end face 18 (FIG. 2) of the base 13 between the cylindrical sockets 19 and 20 is shaped at an angle $\alpha$ equal to $180°-2\theta$.

In this embodiment of the multichannel X-ray spectrometer, $L=76.49$ mm with $R=100$ mm, $\delta = = 5.10^{-4}$ rad., $\theta=22.5°$ and $\theta=135°$ for the spectral line $CuK_\alpha$ of the specimen 5.

But the distance L may be less than $2R (1-2\delta) \sin \theta$. For example $L=76.0$ mm.

The holders 11 (FIG. 2) and 12 are placed into the sockets 19 and 20 as follows.

The cylindrical support 14 of the holder 11 for the crystal analyzer 8 is inserted into the cylindrical socket 19 of the base 13 so that the slit lock 16 grasps the side surfaces 21 of the base 13. The cylindrical support 15 of the holder 12 of the outlet slit 9 is inserted into the cylindrical socket 20 of the base 13 so that the slit lock 17 envelops the side surfaces 21 of the base 13. The axes 22 and 23 of the cylindrical supports 14 and 15 extend respectively through the central generatrix of the crystal analyzer 8 and the outlet slit 9. When the crystal analyzer 8 is turned in the direction of arrows B and C and when the outlet slit 9 is turned in the direction of arrows D and E, the outlet slit is always oriented to the central generatrix of the crystal analyzer 8. Using a screw 25 extending through the body of the base 13 and into the body of the holder 11 of the crystal analyzer 8, the holder 11 can be placed to the assigned Bragg reflection angle.

The multichannel X-ray spectrometer according to the invention operates as follows.

X-radiation from the X-ray tube 2 (FIG. 1) hits the surface of the specimen 5 and excites X-ray fluorescence radiation which passes through the inlet slit 7 of each spectrometric channel 6 and hits the focusing crystal analyzer 8 mounted on an individual holder 11. This crystal analyzer 8 can be turned by the screw 25 to a specific Bragg reflection angle by turning the holder 11 (FIG. 2) with the crystal analyzer 8 in the cylindrical socket 19 of the base 13. This adjustment permits isolation of a specific wavelength from the characteristic X-radiation of the specimen 5. Monochromatic radiation obtained in this manner is focused in the outlet slit 9 and recorded by the detector 10.

Slit locks 16 and 17 are used to achieve precise angular position of the crystal analyzer 8 and the outlet slit 9 in relation to the plane of the focusing circle 24 (FIG. 1). The incident direction of the monochromatic X-radiation emitted by the crystal analyzer 8 (FIG. 2) to the outlet slit 9 is dictated by the angle equal to $180°-2\theta$.

The geometrical condition for focusing X-radiation reflected from the crystal analyzer 8 in the outlet slit 9 is the ratio $L=2R \sin \theta$.

Since the structure of crystals is not ideal, and its mosaic factor ranges from $10^{-2}$ to $10^{-4}$ rad, the geometric condition should allow for this mosaic structure. The final condition for focusing is the ratio $L \leq 2R (1-2\delta) \sin \theta$.

In the multichannel X-ray spectrometer made according to the invention, the distance L (FIG. 2) between the axes 22 and 23 of the cylindrical supports 14 and 15 of the holder 11 for the crystal analyzer 8 and the holder 12 for the outlet slit 9, which coincide with the central generatrix of the crystal analyzer 8 and the outlet slit 9, is equal to or less than $2R (1-2\delta) \sin \theta$, as has been described above.

The multichannel X-ray spectrometer has the following advantages: simple adjustment and small size of spectrometric channels, which simplifies the design of spectrometric channels and the spectrometer as such.

In the description of the preferred embodiment of the invention specific narrow terminology is resorted to for clarity. However, the invention is in no way limited to the terminology thus adopted and it should be remembered that each such term is used to denote all equivalent elements functioning in an analogous way and employed for similar purposes.

While the invention has been described herein in terms of preferred embodiments, numerous variations may be made without departing from the spirit of the invention or the scope of the appended claims, which are easy to understand for those skilled in the art.

These modified forms should be considered as being within the spirit and scope of the invention and the claims.

What is claimed is:

1. A multichannel X-ray spectrometer comprising:

a housing;

an X-ray tube accomodated in said housing and emitting X-radiation;

a specimen holder placed opposite said X-ray tube for holding a specimen exposed to X-radiation and emitting characteristic X-radiation;

spectrometric channels arranged around said X-ray tube and having;

inlet slits arranged to let through said characteristic X-radiation from the specimen;

a base secured in said housing and having a first side surface, a second side surface, and an end face;

focusing crystal analyzers having central generating lines, arranged on a focusing surface having a radius, directly beyond said inlet slits in the direction of said characteristic X-radiation of the specimen and focusing said characteristic X-radiation;

first holders carrying said focusing crystal analyzers and arranged on said base;

outlet slits arranged directly beyond said focusing crystal analyzers in the direction of said characteristic X-radiation of the specimen and allowing passage of said characteristic X-radiation through;

second holders carrying said outlet slits and arranged on said base;

detectors of said characteristic X-radiation, arranged directly beyond said outlet slits in the direction of said characteristic X-radiation of the specimen and receiving said characteristic X-radiation, said first holders being made as first cylindrical supports having first axes and first slit locks;

first cylindrical sockets provided in said end face of said base and arranged to accomodate said first cylindrical supports, said first cylindrical supports being placed in said first cylindrical sockets so that said first slit holders envelop the first side surface and second side surface of said base, said second holders being made as second cylindrical supports having second axes and second slit locks;

second cylindrical sockets made on said end face of said base and arranged to accomodate said second cylindrical supports, said second cylindrical supports being mounted in said second cylindrical sockets so that the second slit locks envelop the first side surface and second side surface of said base, said end face of said base having an angle between the first cylindrical sockets and second cylindrical sockets equal to 180 degrees$-2\theta$, said first axes of said first cylindrical supports, which coincide with said central generating line of said focusing crystal analyzers, and said second axes of said second cylindrical supports, which coincide with said outlet slits, said first axes and said second axes being spaced apart a distance equal to or less than $2R(1-2\delta)\sin\theta$, where R is the radius of said focusing circle of said focusing crystal analyzers, $\delta$ is a mosaic structure factor of the focusing crystal analyzers, and $\theta$ is the Bragg reflection angle.

* * * * *